(12) United States Patent
Burns, Jr. et al.

(10) Patent No.: US 6,669,677 B2
(45) Date of Patent: Dec. 30, 2003

(54) METHOD FOR MANUFACTURING A DISPOSABLE EXCRETA MANAGEMENT DEVICE

(75) Inventors: John Glasgow Burns, Jr., Kobe (JP); Yasuhiro Ishii, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/395,589

(22) Filed: Mar. 24, 2003

(65) Prior Publication Data

US 2003/0204173 A1 Oct. 30, 2003

Related U.S. Application Data

(63) Continuation of application No. PCT/US00/29760, filed on Oct. 27, 2000.

(51) Int. Cl.⁷ .................................................. A61F 13/15
(52) U.S. Cl. .................................. 604/385.19; 604/355
(58) Field of Search ........................... 604/348, 355, 604/385.19

(56) References Cited

U.S. PATENT DOCUMENTS

| 4,804,377 | A |   | 2/1989 | Hanifl |
| 5,865,819 | A | * | 2/1999 | Cisko et al. ............ 604/339 |
| 6,077,254 | A |   | 6/2000 | Silwanowicz |
| 6,106,507 | A |   | 8/2000 | Botten |
| 6,336,920 | B1 | * | 1/2002 | Temple .................... 604/355 |
| 6,491,673 | B1 | * | 12/2002 | Palumbo et al. ............ 604/317 |
| 6,602,233 | B1 | * | 8/2003 | Palumbo et al. ............ 604/335 |
| 6,607,516 | B2 | * | 8/2003 | Cinelli et al. ........... 604/385.19 |
| 2002/0082570 | A1 | * | 6/2002 | Mishima et al. ............ 604/332 |
| 2002/0128614 | A1 | * | 9/2002 | Cinelli et al. ............... 604/332 |
| 2002/0138058 | A1 | * | 9/2002 | Mishima et al. ....... 604/385.19 |

FOREIGN PATENT DOCUMENTS

| EP | 0 140 470 A1 | 5/1985 |
| WO | WO 00/00113 A1 | 1/2000 |

* cited by examiner

Primary Examiner—Weilun Lo
Assistant Examiner—Michael Bogart
(74) Attorney, Agent, or Firm—Kevin C. Johnson

(57) ABSTRACT

A method of manufacturing a disposable excreta management device. The method includes the steps of: combining a continuous liquid impermeable body facing sheet web and a discrete adhesive flange to make a first continuous composite web at a first combining section; forming lateral fold on the continuous liquid impermeable body facing sheet web at a first fold forming section, and then forming a pair of longitudinal folds on the continuous liquid impermeable body facing sheet web at a second fold forming section; combining the first continuous composite web and a continuous liquid impermeable garment facing sheet web to make a second continuous composite web at a second combining section, and cutting the second continuous composite web into the discrete disposable excreta management device.

9 Claims, 17 Drawing Sheets

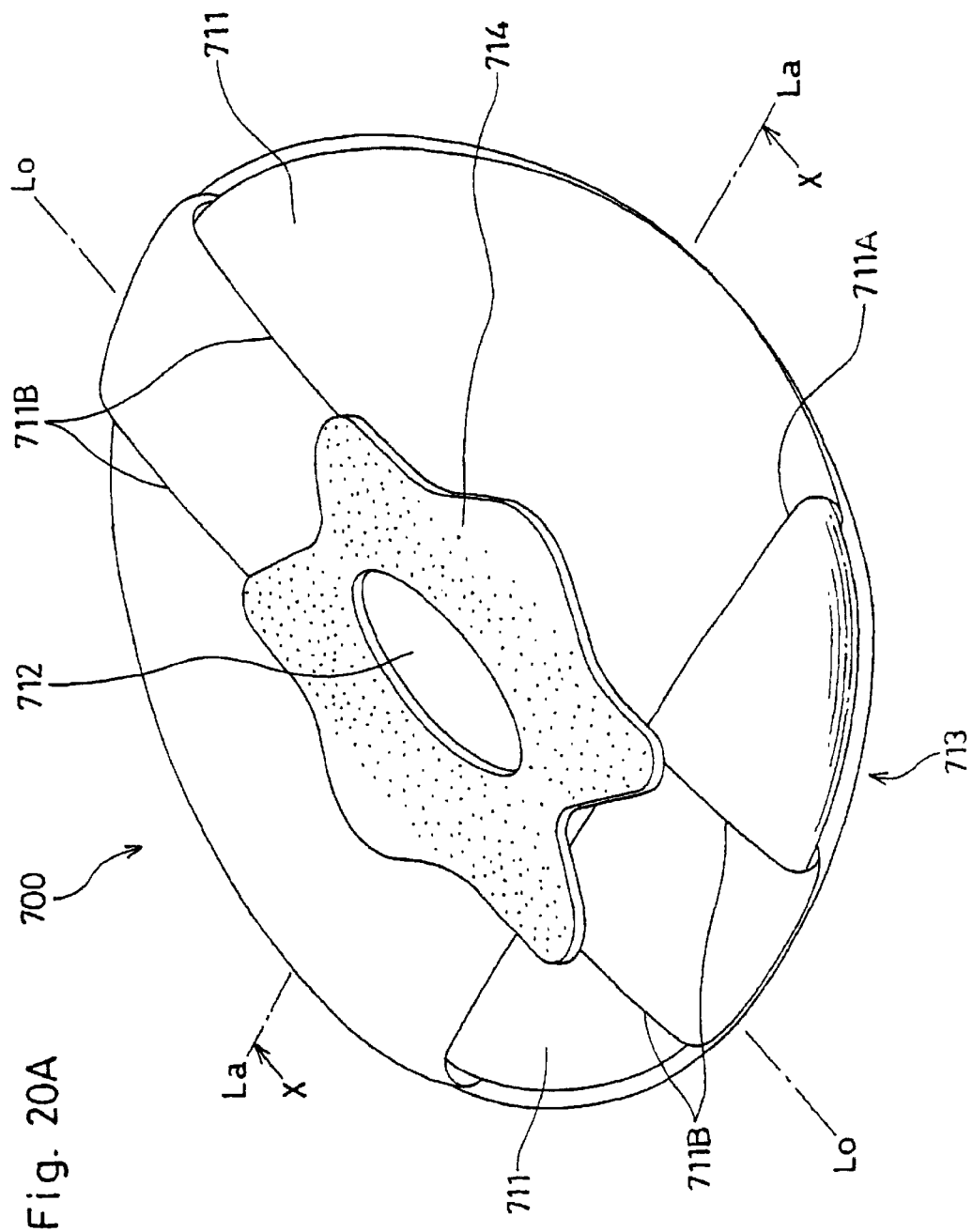

METHOD FOR MANUFACTURING A DISPOSABLE EXCRETA MANAGEMENT DEVICE

CROSS REFERENCE TO RELATED REFERENCES

This is a continuation of International Application PCT/US00/29760 with an International filing date of Oct. 27, 2000.

FIELD OF THE INVENTION

This invention relates to disposable excreta management devices, and more particularly, to a method for manufacturing disposable excreta management devices.

BACKGROUND

Disposable excreta management devices in the form of excreta incontinence protection devices or in the form of excreta collection devices for medical purposes are known in the art.

Representative devices of the former type are disclosed in, e.g. EP 0 140 470. It discloses disposable devices which include a water-impervious barrier sheet formed as a bag, an opening to be located next to the wearer's uro-genital area to receive the discharged urine, and containing an absorbent material to absorb the discharged urine. EP 0 140 470 additionally discloses the presence of a wicking layer between the opening and the absorbent material.

Representative urine collector devices are disclosed in, e.g., U.S. Pat. No. 4,804,377. It discloses a urine collector device for infants or small children having a flexible collection bag and an adhesively-faced attachment member joined to the bag.

Representative urine collector devices containing an absorbent material are disclosed in, e.g., WO 00/00113. It discloses a urine collector device for infants or adults, furthermore, for bedridden patients or active patients, having a flexible collection bag, an adhesive flange joined to the bag and an absorbent material to be contained within the bag. The device is a superior disposable urine management device which has a long wear period and ensures perfect fit and conformance to the wearer. Additionally, the device is designed to be worn instead of a diaper by a baby, small child or incontinent adult.

However, none of these publications disclose a method for manufacturing such an above-mentioned superior disposable excreta management device efficiently.

It is an object of the present invention to provide a method for manufacturing a disposable excreta management device.

Another object of the present invention is to provide a method for manufacturing a disposable excreta management device having a plurality of folds on the surface of the liquid impermeable body facing sheet.

A further object of the present invention is to provide a method for manufacturing a disposable excreta management device having a hydrogel adhesive to attach the device to wearer's body.

SUMMARY

The present invention relates to a method of manufacturing a disposable excreta management device comprising a liquid impermeable body facing sheet having an opening, a liquid impermeable garment facing sheet, and an adhesive flange provided adjacent to the opening for releasable attachment to the body of the wearer. The adhesive flange comprises a substrate layer and an adhesive layer. The liquid impermeable body facing sheet has plural folds thereon. The plural folds comprises at least one lateral fold and at least a pair of longitudinal folds. The method comprising the steps of: combining a continuous liquid impermeable body facing sheet web and a discrete adhesive flange to make a first continuous composite web at a first combining section; forming lateral fold on the continuous liquid impermeable body facing sheet web at a first fold forming section, and then forming a pair of longitudinal folds on the continuous liquid impermeable body facing sheet web at a second fold forming section; combining the first continuous composite web and a continuous liquid impermeable garment facing sheet web to make a second continuous composite web at a second combining section, and cutting the second continuous composite web into the discrete disposable excreta management devices.

BRIEF DESCRIPTION OF THE DRAWINGS

While the Specification concludes with claims which particularly point out and distinctly claim the invention, it is believed the present invention will be better understood from the following description of preferred embodiments taken in conjunction with the accompanying drawings, in which like reference numerals identify identical elements and wherein:

FIG. 20A is a perspective view of another embodiment of a disposable excreta management device.

DETAILED DESCRIPTION

All cited references are incorporated herein by reference in their entireties. Citation of any reference is not an admission regarding any determination as to its availability as prior art to the claimed invention.

The definitions of several terms are first provided to assist the reader in understanding the present invention.

The term "comprising" means that other steps and other ingredients which do not affect the end result can be added. This term encompasses the term "consisting of" and "consisting essentially of". The term "disposable" as used herein describes devices which generally are not intended to be laundered or otherwise restored or reused (i.e., they are intended to be discarded after a single use and, preferably, to be recycled, composted or otherwise disposed of in an environmentally compatible manner.) The term "nonwoven", as used herein, refers to fabrics made of fibers held together by interlocking or bonding which are not woven, knitted, felted, or the like. (The term "fabric", as used herein, may refer to a nonwoven web, a woven material, or other types of fabrics.) The term "longitudinal", as used herein, refers to a line, axis or direction in the plane of the disposable excreta management device that is generally aligned with (e.g., approximately parallel to) a vertical plane which bisects a standing wearer into left and right body halves when the disposable excreta management device is worn. The terms "transverse" or "lateral" used herein, are interchangeable, and refer to a line, axis or direction which lies within the plane of the disposable excreta management device that is generally perpendicular to the longitudinal direction.

All percentages are by weight of total composition unless specifically stated otherwise.

The present invention, in its product and process aspects, is described in detail as follows.

Figure 1:
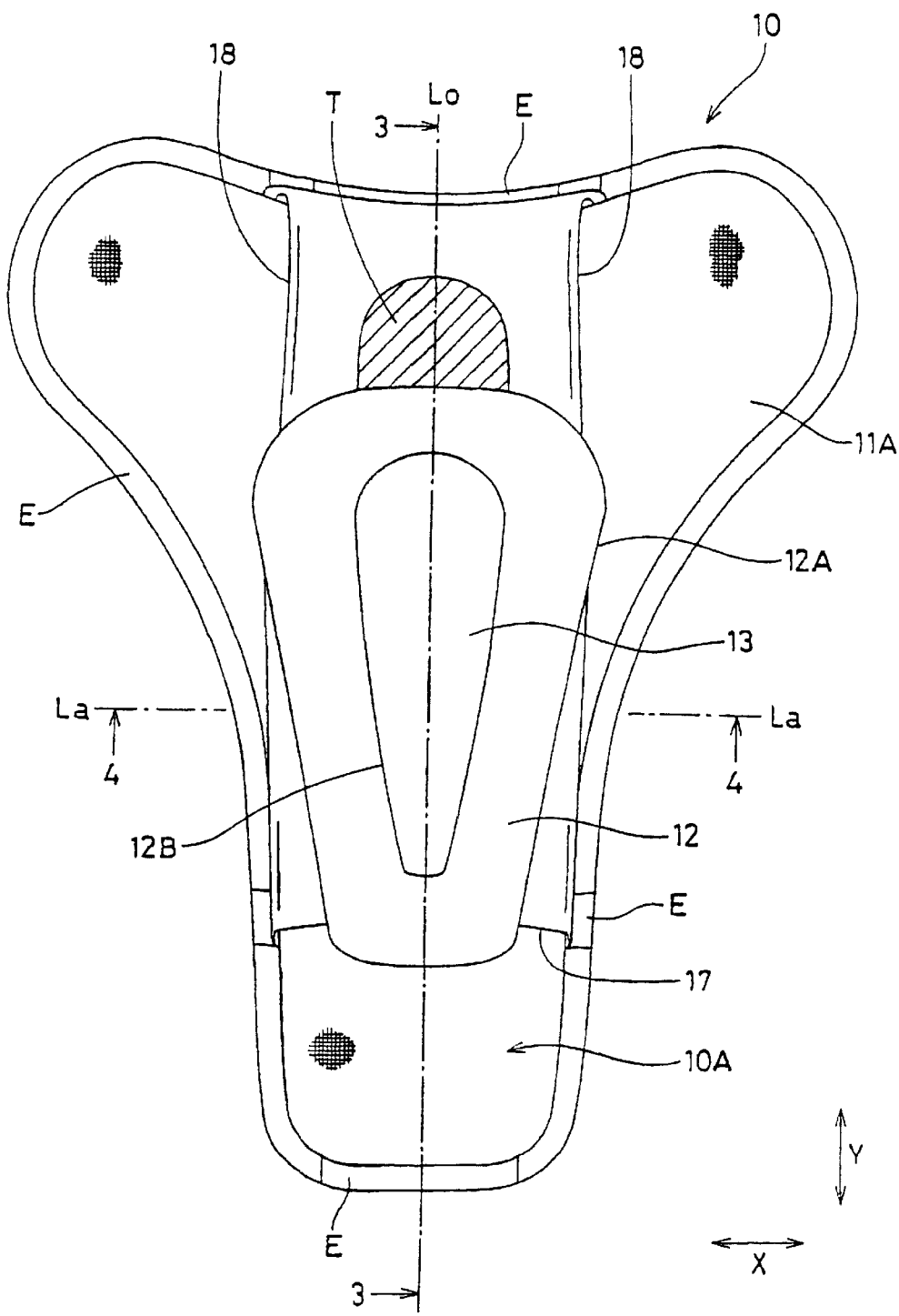
FIG. 1 is a top plan view of one embodiment of a disposable excreta management device produced by a method of the present invention.
Figure 2:
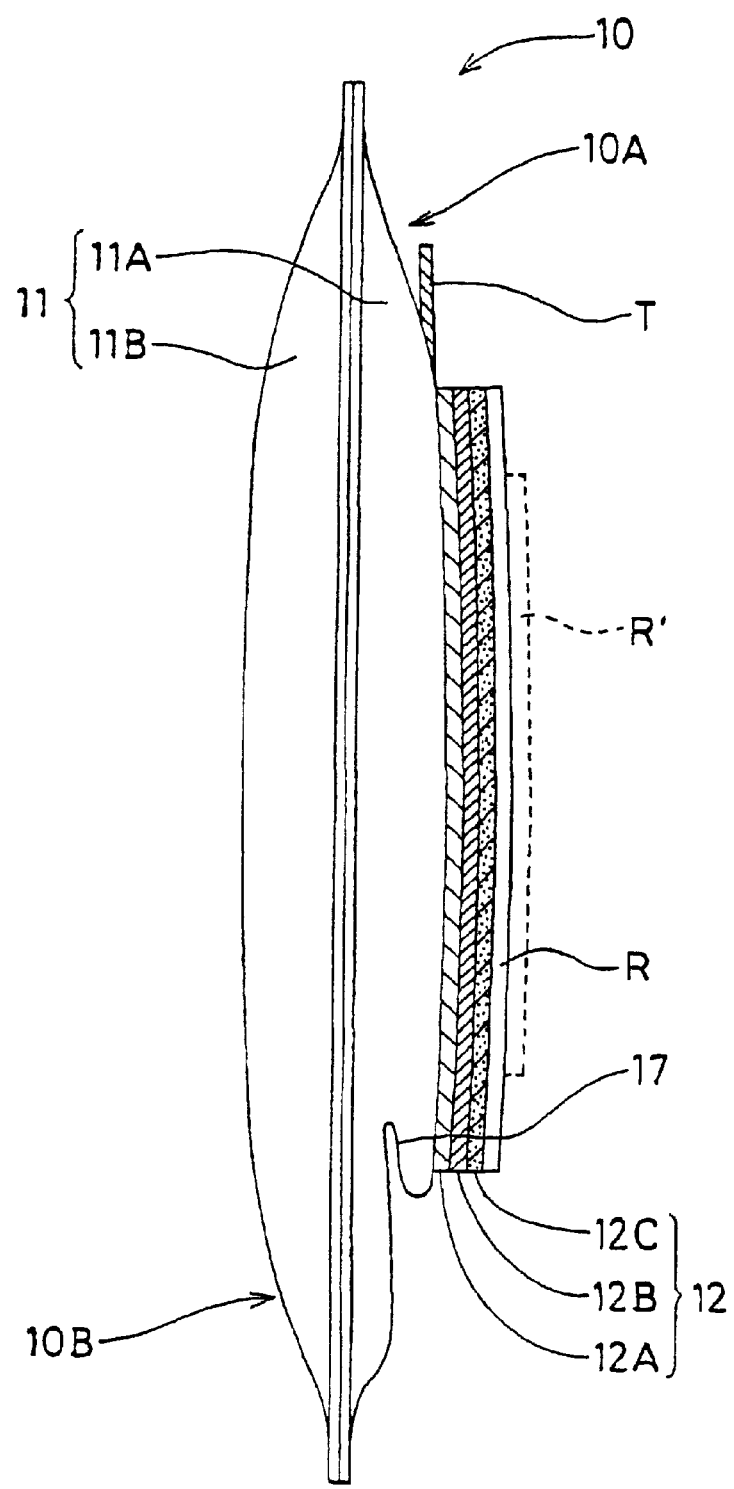
FIG. 2 is a side view of the disposable excreta management device of FIG. 1.
Figure 3:
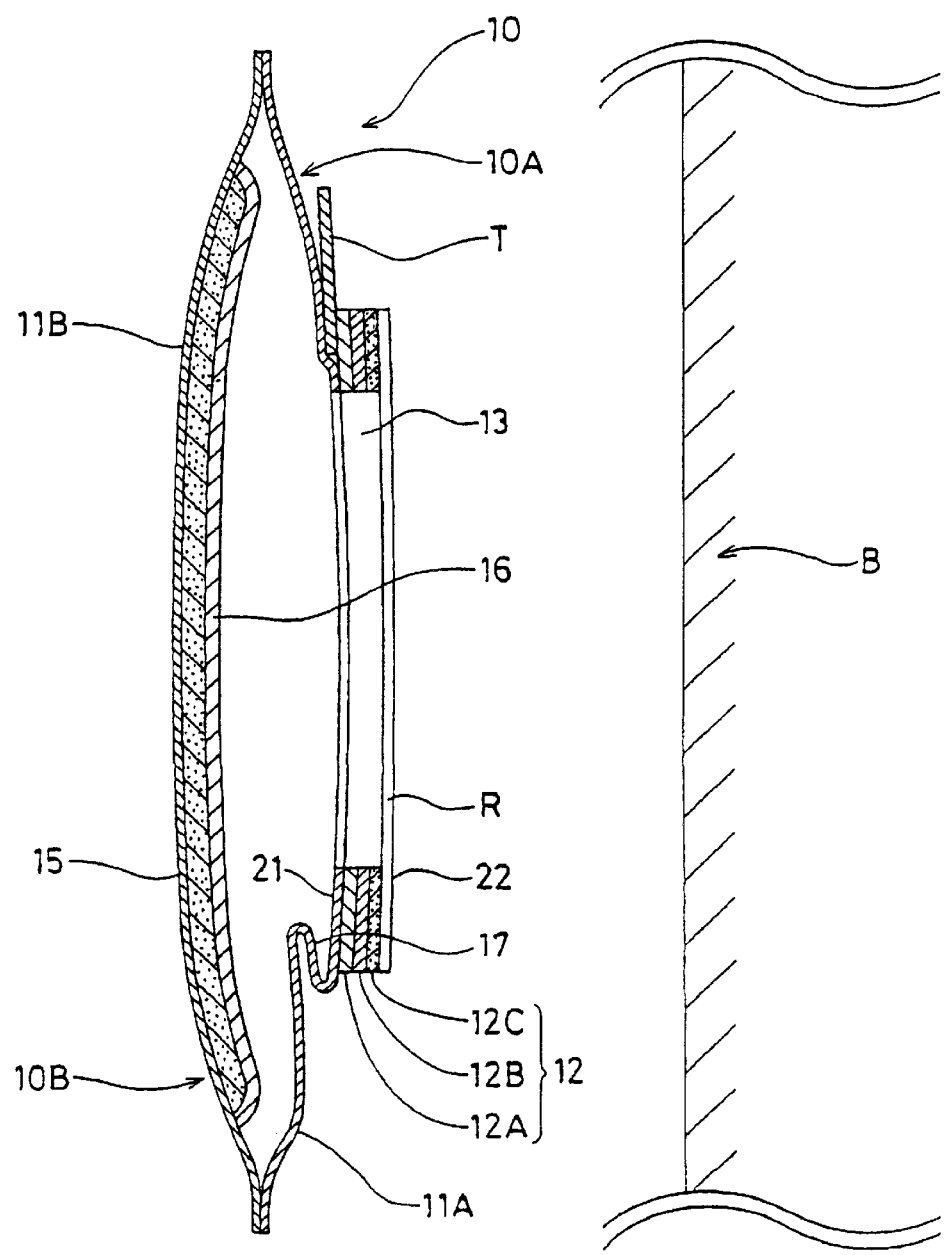
FIG. 3 is a cross-sectional view taken along line 3—3 of FIG. 1.
Figure 4:
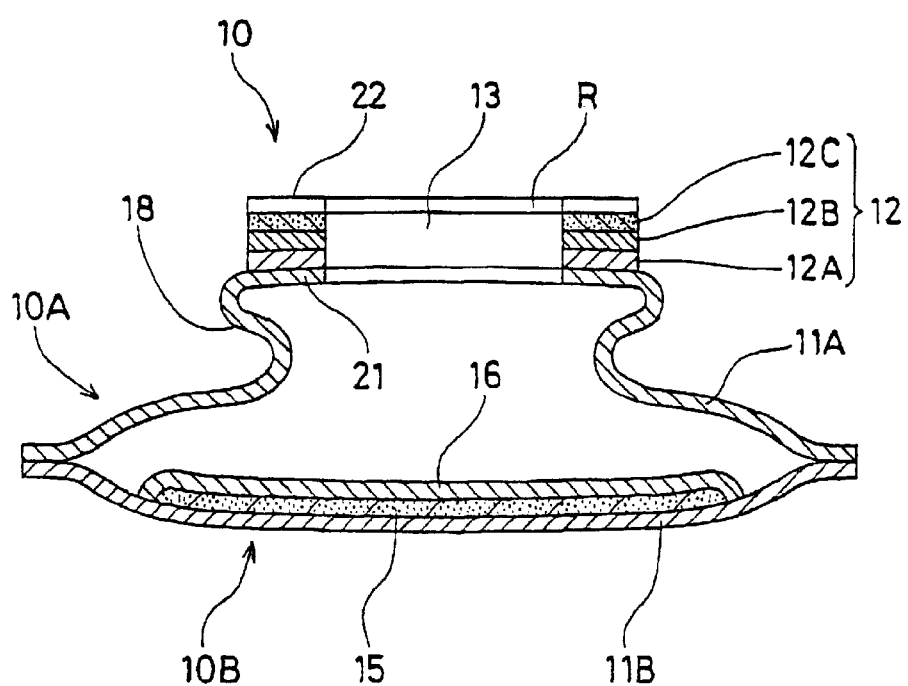
FIG. 4 is a cross-sectional view taken along line 4—4 of FIG. 1.

Referring now to FIGS. 1–4, there is shown a preferable embodiment of a disposable excreta management device of the present invention, such as a disposable urine management device (10). The top plan view of the device (10) is shown in FIG. 1. The side view of the device (10) is shown in FIG. 2. The cross-sectional view of the device (10) taken along the 3—3 line of the FIG. 1 is shown in FIG. 3. The cross-sectional view of the device (10) taken along the 4—4 line of the FIG. 1 is shown in FIG. 4. The disposable urine management device (10) has two centerlines, one is a longitudinal centerline (Lo) and the other is a lateral centerline (La). The device (10) has two surfaces, one is a body facing surface (10A) and the other is a garment facing surface (10B). The disposable urine management device (10) comprises a bag (11) having an opening (13) and a flange (12) surrounding the opening (13).

The bag (11) as used herein is a flexible receptacle for the containment of discharged excreta such as urine and/or bowel movement. The bag (11) can be provided in any shape or size depending on the intended use thereof, i.e. whether the device is intended for bedridden patients or active patients suffering from incontinence. For example elongated bags which are principally tubular or rectangular are typically utilized by bedridden patients and elderly incontinence sufferers. For more active wearers whether infants or adults, the urine management device should preferably be anatomically shaped such that the device follows the contours of the body and can be worn inconspicuously by the wearer under normal garments. Particularly, preferred shapes are flat circular and flat T shaped type bags, triangle shaped bags, cone shaped bags, truncated cone shaped bags and pyramidal or truncated pyramidal shaped bags. In a preferred embodiment shown in FIG. 1, the bag (11) has a substantially triangle shape with three rounded corners. In addition, the bag (11) is preferably shaped to fit the uro-genital region of the wearer to ensure good contact between the flange (12) and the skin of the wearer.

The bag (11) is preferably designed to provide sufficient volume for urine under a variety of wearing conditions, also when worn by a freely moving, i.e., not bedridden wearer. The bag (11) is designed to safely contain any entrapped material, typically it will be liquid impermeable, yet it may be breathable. The bag is designed of sufficient strength to resist rupturing in use.

Depending on the shape of the bag (11) required, the bag may be made from a unitary piece of material or from a number of separate pieces of material, which may be identical or different and which are sealed at their respective peripheries.

The bag (11) can comprise one or multiple layers, preferably two or three layers. The layer on the inside of the bag, which will typically at least partially come in contact with urine is called the inner layer. The outermost layer of the bag (11), which will typically at least partially come in contact with the skin of the wearer and the garments of the wearer, is called the outer layer.

The layers of the bag material may be provided from any material so that the bag is liquid impervious. The layers may in particular comprise any material such as nonwovens or films. In a preferred embodiment; the layers may be formed from a nonwoven layer and a film. The outer layer of the bag (11) is preferably provided with a nonwoven layer. Such material layers present an uneven surface to the skin of the wearer and thus reduce significantly the problem of occlusion and greatly improve skin healthiness. In one preferred embodiment, the bag (11) comprises two layers. Preferably the outer layer comprises a nonwoven layer and the inner layer comprises a film. Alternatively, the bag (11) comprises three layers; one film layer and two nonwoven layers. The film may be interposed between the two nonwoven layers. This sequence of layers results in a closed fibrous structure, which has a particularly pleasing sensation on contact with the skin of the wearer.

Suitable nonwoven layers may comprise felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, combinations of the above or the like.

The nonwoven layer or the nonwoven layers constituting the bag (11) may be hydrophobic or hydrophilic. For example, if the bag comprises a film layer, the nonwoven layers may be hydrophilic or hydrophobic. If the bag does not comprise a film layer, preferably at least one nonwoven layer is hydrophobic. It may even be desirable to make both nonwoven layers hydrophobic to ensure that the bag is liquid impervious.

Typically, the nonwoven layer is treated with a surface active material, such as a fluorchemical or other hydrophobic finishings, to provide the requisite hydrophobicity. The nonwoven layer, however, may equally be treated with coatings of liquid impervious materials such as hot-melt adhesives or coatings of silicone or other hydrophobic compounds such as rubbers and vegetable and mineral waxes or it may be physically treated using nanoparticulates or plasma coating techniques, for example.

The nonwoven layer can also be treated with agents to improve the tactile perceivable softness. The agents include but are not limited to vegetable, animal or synthetic oils, silicone oils and the like. The presence of these agents are known to impart a silky or flannel-like feel to the nonwoven layer without rendering it greasy or oily to the tactile sense of the wearer. Additionally, surfactant material, including anionic, non-anionic, cationic and non-cationic surfactants, may be added to further enhance softness and surface smoothness.

Furthermore, the nonwoven layer may be impregnated with a lotion to provide desirable therapeutic or protective coating lotion benefits. The lotion coating is transferable to the skin of the wearer by normal contact and wearer motion and/or body heat. Generally, mineral oil in the form of a lotion is recognized as being effective in imparting a soothing, protective coating to the skin of the wearer. It is also possible to impregnate the nonwoven layer with a solid oil phase of cream formulation or to incorporate into the nonwoven layer an array of pressure- or thermal- or hydrorupturable capsules containing for example, baby oil.

Suitable film materials may comprise a thermoplastic material. The thermoplastic material can be selected from among all types of polyolefins especially polyethylene, polypropylene, amorphous polyolefins, and the like; material containing meltable components comprising fibers or polymeric binders including natural fibers such as cellulose-wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Chemical Co., Japan under the designation ESPOIR NO; and monolithic breathable materials such as Hytrel™ available from DuPont and Pebax™ available from ELF Atochem, France. In a preferred embodiment, a film, which is comprised in any layer, is preferably permeable to gases such as air and to vapour such as water vapour in order to avoid the problem of entrapment and condensation of moisture vapour given off by the body of the wearer and thus, the hot, clammy and uncomfortable conditions after a short period of use.

In the embodiment as shown in FIGS. 1–4, the bag (11) preferably comprises a liquid impermeable body facing sheet (11A) positioned on the body facing side (10A) and a liquid impermeable garment facing sheet (11B) positioned on the garment facing side (10B). Both the body facing sheet (11A) and the garment facing sheet (11B) comprise a polyethylene/polypropylene film and a nonwoven which is laminated on the outside surface of the film.

The body facing sheet (11A) is folded (tacked) so that the body facing sheet (11A) can expand vertically to have a 3-dimentional shape in use, thereby ensuring better wearing comfort for a moving wearer and providing extra storage capacity in use if needed. The body facing sheet (11A) preferably has a fold (17) having an alphabet "Z"-like configuration in the cross-sectional view of the body facing sheet taken along the direction at an angle with the direction in which the fold extends as shown in FIG. 2 and 3. Such a fold is referred to as "Z-fold" herein. In the embodiment as shown in FIGS. 1–4, the body facing sheet (11A) preferably has one Z-fold (17) oriented in the lateral direction (X). Alternatively, the Z-fold may be oriented at an angle to the lateral direction (X). The body facing sheet (11A) also has two Z-folds (18) oriented in the longitudinal direction (Y). Preferably, the two Z-folds (18) disposed oppositely with respect to the longitudinal centerline (Lo) and parallel to the longitudinal centerline (Lo). Alternatively, the two Z-folds (18) may be disposed at an angle with respect to the longitudinal centerline (Lo). The combination of the two opposite Z-folds has a Greek letter "Ω" like configuration in the cross-sectional view of the body facing sheet taken along the direction at an angle with the direction in which the folds extend as shown in FIGS. 1 and 4. Such a combination of two opposite Z-folds is referred to as "Ω-fold (OMEGA-fold)" herein. Thus, the body facing sheet (11A) in this embodiment comprises one Z-fold (17) and one OMEGA-fold (18) as shown in FIG. 1. Furthermore, the number of Z-fold and/or OMEGA-fold on the body facing sheet (11A) is not limited to the embodiment as shown in FIG. 1 as far as the body facing sheet (11A) can expand vertically to have a 3-dimentional shape in use.

As shown in FIG. 1, the body facing sheet (11A) is provided with an opening (13) whereby excreta such as urine and/or bowel movement is received from the body prior to storage within the bag cavity. The opening (13) is surrounded by a flange (12) and may be provided in any shape or size, such as circular, oblong, heart shaped and may be symmetrical or asymmetrical, preferably the opening has an oblong configuration either in the longitudinal or in the transversal direction.

As shown in FIGS. 1–4, the flange (12) (or adhesive flange) is provided at the periphery of the opening (13) to attach the device (10) to the wearer's body (B). The adhesive flange (12) has a wearer body facing side (22) and an opposed garment facing side (21) as shown in FIGS. 3 and 4. Furthermore, the adhesive flange (12) has an outer periphery (12A) and an inner periphery (12B) as shown in FIG. 1. In a preferred embodiment, these are two large, substantially flat surfaces of the adhesive flange (12). The adhesive flange (12) may be provided in any size depending on the wearer group for which the device is intended. The adhesive flange (12) may be provided in any shape and preferably has a symmetrical, slightly oblong shape.

In the embodiment as shown in FIGS. 1–4, the adhesive flange (12) may comprise a nonwoven layer (12A), a polyurethane layer (12B) and an adhesive layer (12C) in its order from the body facing sheet (11A) towards the wearer's body (B) as shown in FIG. 3. In this embodiment, both the nonwoven layer (12A) and the polyurethane layer (12B) may be provided as a substrate in order to support the adhesive layer (12C), or a substrate may comprise either of them. Particularly, the polyurethane layer (12B) may be provided in order to adapt the devise (10) to the movement of the wearer during use of the device (10).

The adhesive flange (12) should be made of soft, flexible and malleable material to allow easy placement of the flange to the uro-genital area. In addition, the adhesive flange (12) may be made of a hydrophobic material such that if urine does come into contact with the perimeter surrounding opening (13) it is repelled and does not wick to the outer edge of the adhesive flange (12). It is also desirable to construct the adhesive flange (12) from a breathable material to avoid the problem of entrapment and condensation of moisture vapor given off by the body of the wearer and thus, the hot, clammy and uncomfortable conditions after a short period of use. Suitable materials for the adhesive flange (12) include but are not limited to nonwoven materials, and foams, such as open celled thermoplastic foams. An open-cell foam having a thickness within the general range of about 0.5 to 10 millimeters (preferably about 2 millimeters) has been found particularly effective. Other foam materials or other suitable plastics sheet materials having the described properties of such foams (i.e., softness, pliability, stretchability, contractability, breathability, and hydrophobicity) might be used.

The body facing side (22) of the adhesive flange (12) comprises a body-compatible adhesive such as the adhesive layer (12C) as shown in FIGS. 2–4. The adhesive layer (12C) is used in order to fix the device (10) with the wearer's body (B). In the embodiment as shown in FIGS. 1–4, the adhesive layer (12C) is preferably covered with a release film (R) to protect the adhesive layer (12C) from contamination before use, such as siliconized paper or film. For the manufacturing reason, if the opening (13) is formed thorough the release film (R), a second release film (R') designated by the broken line in FIG. 2 may be added so that foreign objects do not enter into the bag (11) before use of the device (10). The adhesive layer (12C) may cover the entire body facing surface of the flange, or alternatively have at least one, preferably two to six non-adhesive portions. These portions may be adhesive free or may contain inactivated or covered adhesives. Before application of the urine management device (10) to the skin of the wearer, the release means if present is removed.

Preferably, a tab (T) is applied on the adhesive flange (12) in order to remove the device (10) from the wearer's body (B) easily. The tab (T) helps users remove the device (10) from the wearer's body.

Any medically approved water resistant pressure sensitive adhesive may be used for the adhesive layer (12C) to attach the device to the uro-genital area of the wearer, such as hydrocolloid adhesives and hydrogel adhesives. Particularly effective adhesives in providing the desired adhesive properties to secure the flange to the skin of the wearer at the sensitive uro-genital area, whilst allowing for relatively painless application and removal are hydrophillic hydrogels formed from crosslinking polymers with a plastisicer to form a 3-dimensional matrix.

The adhesive can be applied to the body facing side (22) of the adhesive flange (12) by any means known in the art such as slot coating, spiral, or bead application or printing. Typically the adhesive is applied at a basis weight of from 20 g/m$^2$ to 2500 g/m$^2$, preferably from 500 g/m$^2$ to 2000 g/m$^2$, more preferably from 700g/m$^2$ to 1500 g/m$^2$ depending on the end use envisioned. For example for urine management devices to be used for children the amount of adhesive may be less than for urine management devices designed for active adult incontinence sufferers.

The adhesive flange (12) is attached to the body facing sheet (11A) by means known to the man skilled in the art, such as adhesives.

An absorbent material (15) is contained within the bag (11). I.e., the absorbent material (15) is positioned between the body facing sheet (11A) and the garment facing sheet (11B) as shown in FIGS. 3 and 4. The absorbent material (15) may be positioned in the bag (11) in any suitable manner. For example, the absorbent material (15) may be loosely arranged within the bag (15) or may be secured to the inner side of the garment facing sheet (11B). Any known techniques for securing absorbent material to nonwoven and film substrates may be used to secure the absorbent material (15) to the inner layer of the bag. The absorbent material may also be arranged to have any desired shape or configuration (e.g., rectangular, oval, circular, etc.). The absorbent material (15) may comprise any absorbent material which is capable of absorbing and retaining liquids such as urine. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers, synthetic fibers such as crimped polyester fibers; peat moss; tissue, including tissue wraps and tissue laminates; absorbent foams; absorbent sponges; superabsorbent polymers; superabsorbent hydrogel-forming polymeric material; absorbent gelling materials; or any other known absorbent material or combinations of materials or mixtures of these. The configuration and construction of the absorbent component may also be varied (e.g., the absorbent component may have varying caliper zones (e.g., profiled so as to be thicker in the center), hydrophilic gradients, superabsorbent gradients, or may comprise one or more layers or structures.

In the embodiment, the device (10) also has a liquid-permeable topsheet (16) to cover the absorbent material (15) as shown in FIGS. 3 and 4. The liquid impermeable body facing sheet (11A), the liquid-permeable topsheet (16) and the liquid-impermeable garment facing sheet (11B) are preferably joined at the periphery edge (E) of the device (10) by any means known in the art such as a heat seal.

The liquid-permeable topsheet (16) is preferably compliant, soft feeling, and non-irritating to the wearer's skin. A suitable liquid-permeable topsheet (16) may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The liquid-permeable topsheet (16) is preferably made of a hydrophobic material to isolate the wearer's skin from body fluids (e.g. urine) which have absorbed in the absorbent material (15). However, in case body fluid discharged from the wearer is accidentally deposited on the liquid-permeable topsheet (16), at least the upper surface of the liquid-permeable topsheet (16) may be treated to be hydrophilic so that liquids will transfer through liquid-permeable topsheet (16) more rapidly. This diminishes the likelihood that body fluid will flow off the liquid-permeable topsheet (16) rather than being drawn through the liquid-permeable topsheet (16) and being absorbed by the absorbent material (15). The liquid-permeable topsheet (16) can be rendered hydrophilic by treating it with a surfactant. Suitable methods for treating the liquid-permeable topsheet (16) with a surfactant include spraying the liquid-permeable topsheet (16) material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991. Alternatively, surfactant may be impregnated into the fibers or resin and the topsheet 28 may be formed by the fibers with impregnated surfactant.

The process for manufacturing a disposable excreta management device is described herein below.

The definitions of several terms are first provided to assist the reader in understanding the method or process. The term "machine direction" (hereinafter "MD") refers to that direction which is parallel to the flow of the materials (e.g. materials (211), (311) and (411) of the present invention). The direction (MD) is indicated by arrows in FIG. 5. The term "cross-machine direction" (hereinafter "CD") is perpendicular to the machine direction.

The term "Z-fold" as used hereinafter refers to folds oriented in the lateral direction (X) as shown in FIG. 1, and the term "OMEGA-fold" as used hereinafter refers to a pair of opposite Z-folds oriented in longitudinal direction (Y) as shown in FIG. 1.

Figure 5:
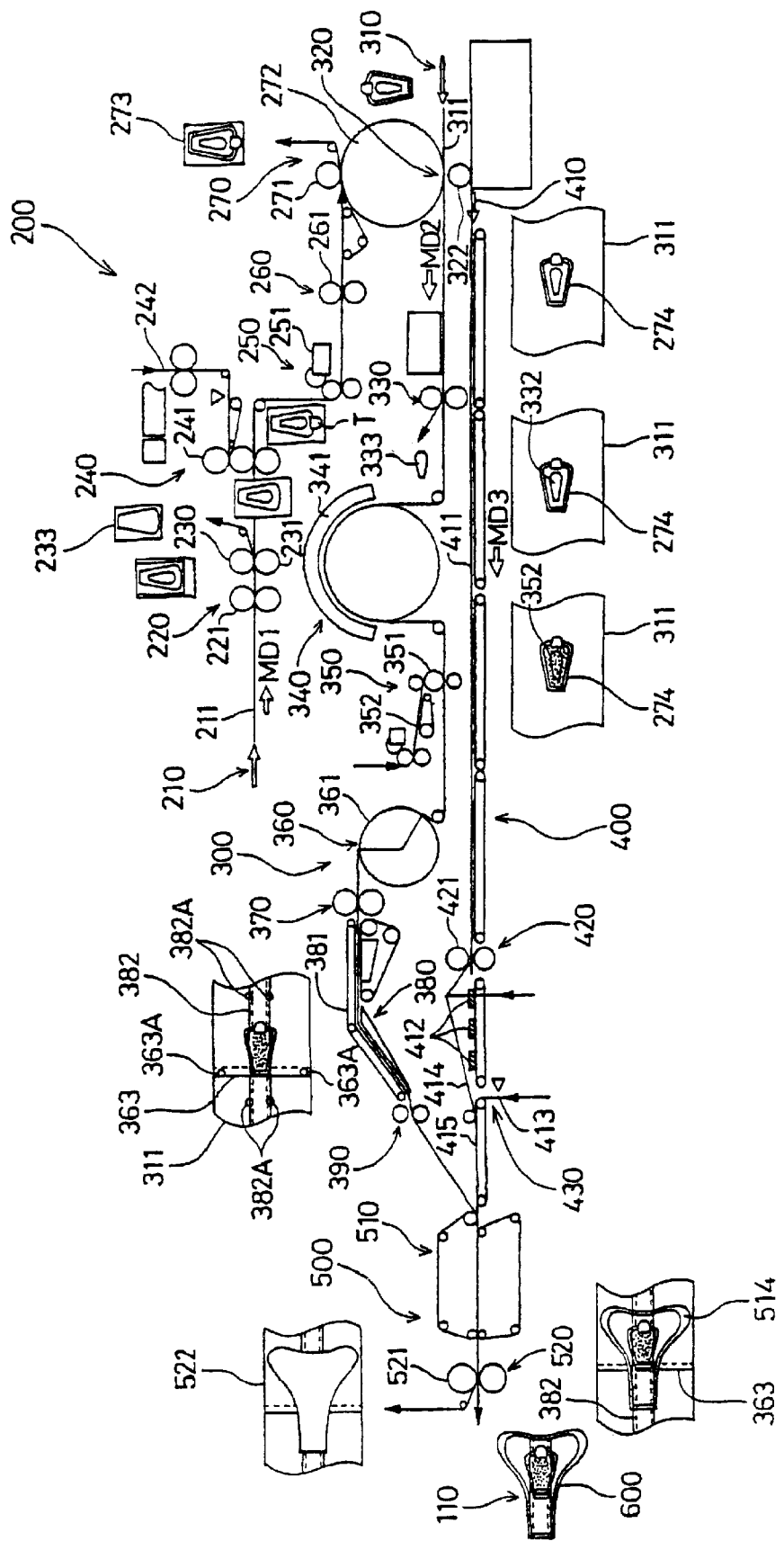
FIG. 5 is a schematic side elevational view of an exemplary embodiment of the process of the present invention.

The process for manufacturing the disposable urine management device (10) of the present invention is shown in FIG. 5. The process comprises four major sections in the process, "an adhesive flange making section (200)", "a body facing sheet making section (300)", "an absorbent material making section (400)" and "the final product making section (500)".

The adhesive flange making section (200) comprises seven steps, a flange material feeding step (210), a pattern embossing step (220), an outer flange cutting step (230), a tab attaching step (240), a glue applying step (250), a release film perforating step (260) and a release film trimming step (270).

Figure 6:
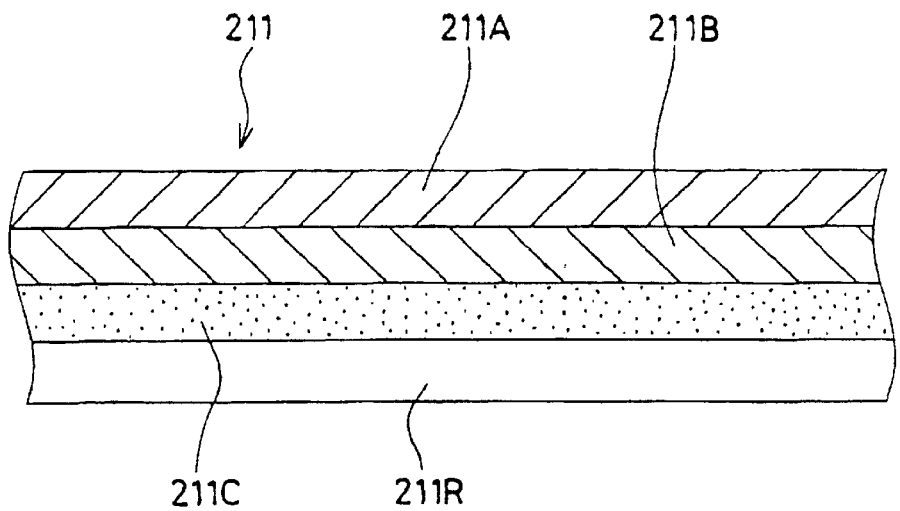
FIG. 6 is an enlarged cross-sectional view of a continuously formed flange material.

The flange material feeding step (210) continuously feeds an unwound continuous flange material (211) toward the pattern embossing step (220) along MD1. As shown in FIG. 6, the continuous flange material (211) preferably comprises the multi-layer structure comprising a nonwoven layer (211A), a polyurethane layer (211B), a hydrogel adhesive layer (211C) and a release film layer (211R).

Figure 7:
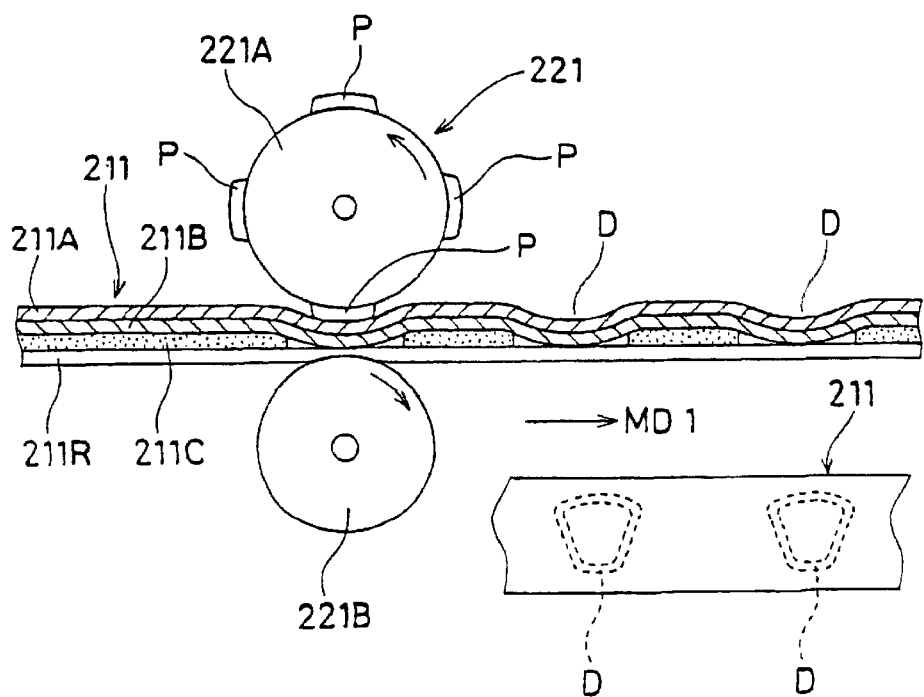
FIG. 7 is a fragmentary, schematic side elevational view of the pattern embossing unit shown in FIG. 5.

The pattern embossing step (220) forms discrete concave areas (D) on the continuous flange material (211) as shown in FIG. 7. The pattern embossing step (220) may include a pattern embossing unit (221). The pattern embossing unit (221) has a patterned roll (221A) and a back-up roll (221B) as shown in FIG. 7. The patterned roll (221A) has plural patterned protrusions (P) on the surface of itself. The shape of a patterned protrusion may substantially correspond to the outer periphery (12A) of the adhesive flange (12) in FIG. 1. One of or both of the patterned roll (221A) and/or the back-up roll (221B) are biased toward each other with a predetermined pattern-element loading at the nip between the rolls (221A) and (221B). By feeding the continuous flange material (211) to the nip of the pattern embossing unit (221) as shown in FIG. 7, the discrete concave areas (D) are formed into the hydrogel adhesive layer (211C) by the patterned protrusions (P). A pattern of the discrete concave areas (D) corresponds to the pattern of the protrusions (P) of the patterned roll (221A). The pattern of the protrusions (P) may substantially correspond to a shape of the outer periphery (12A) of the adhesive flange (12) in FIG. 1. In this step, because the hydrogel layer (211C) has fluidity, the hydrogel layer (211C) is pushed aside at the discrete concave areas (D) of the continuous flange material (211) by the compression of the patterned protrusions (P). Accordingly, the hydrogel layer (211C) does not exist or at least a majority of the hydrogel is removed at the discrete concave areas (D) of the continuous flange material (211) after passing through the nip between the rolls (221A) and (221B). This allows a stable and easy operation to cut the continuous flange material (211) in the outer flange cutting step (230). The continuous flange material (211) is then fed toward the outer flange cutting step (230) along MD1.

Figure 8:
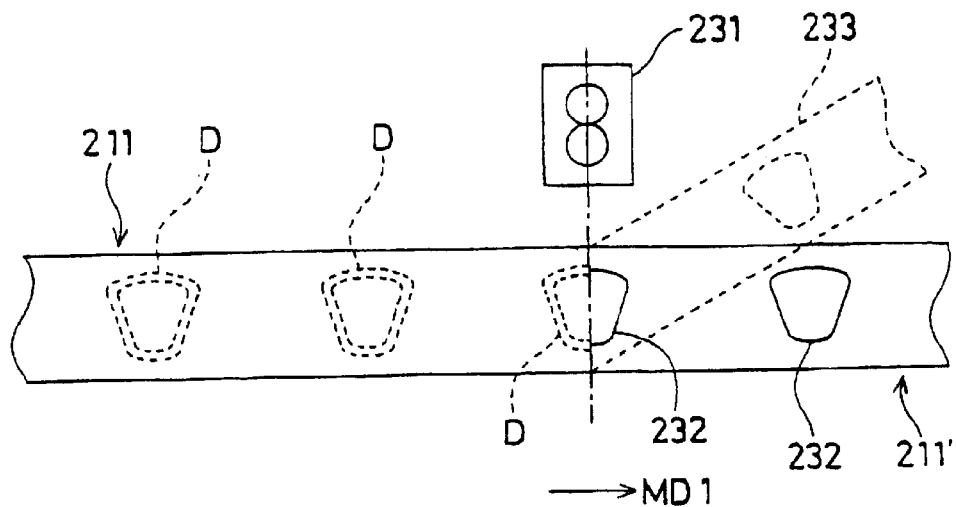
FIG. 8 is a fragmentary plan view of the outer flange cutting step which is a part of the process in FIG. 5.

The outer flange cutting step (230) may include a cutting unit (231). In the outer flange cutting step (230), the continuous flange material (211) is forwarded to the cutting unit (231) and is cut into a discrete segment having an outline shape of the adhesive flange part (232) and then the unnecessary part (233) is trimmed as shown in FIGS. 5 and 8. The outline shape of the adhesive flange part (232) corresponds to the outer periphery (12A) of the adhesive flange (12) in FIG. 1. The cutting unit (231) may have a conventional cutter having a die cutter. Alternatively, any other known method to cut may be used. In this step, the hydrogel adhesive layer (211C), the polyurethane layer (211B) and the nonwoven layer (211A) may be cut by the cutting unit (231), but only the release film layer (211R) may not be cut. This allows the discrete adhesive flange part (232) to stay on the release film layer (211R) after this step. The continuous flange material (211') is then fed toward the tab attaching step (240) along MD1.

The tab attaching step (240) puts the removal tab (T) (refer to FIG. 4) to the discrete adhesive flange part (232) of the continuous flange material (211'). The tab attaching step (240) may include a tab-flange material joining unit (241) as shown in FIG. 5. The continuous tab material (242) is fed toward the tab-flange material joining unit (241). The continuous tab material (242) is cut into a discrete segment having a final tab shape and is applied glue on the way to the tab-flange material joining unit (241). Finally, the tabs (T) are applied on the discrete adhesive flange parts (232) on the continuous flange material (211') at the tab-flange material joining unit (241). Then the continuous flange material (211') is fed toward the glue applying step (250) along MD1.

Figure 9:
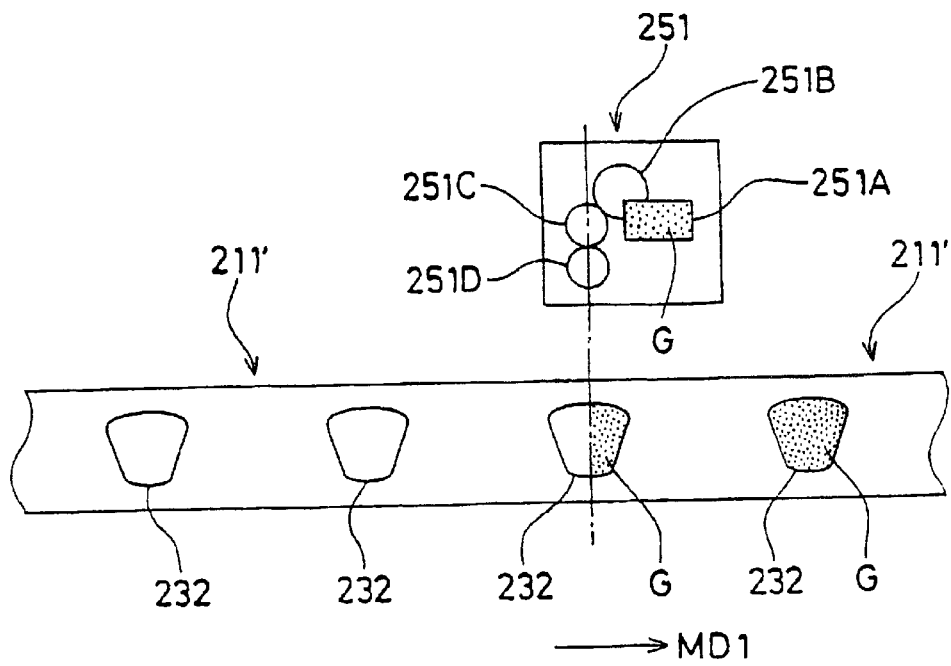
FIG. 9 is a fragmentary plan view of the glue applying step which is a part of the process in FIG. 5.

The glue applying step (250) applies the glue (G), for attaching the adhesive flange on the body facing sheet (311), to the adhesive flange part (232) of the continuous flange material (211') as shown in FIG. 9. The glue applying step (250) may include the graphic pattern unit (251) (hereinafter "GP unit"). The GP unit (251) is a glue applicator which is possible to apply a patterned glue, and has a glue pan (251A), a distribution roll (251B), a patterned roll (251C) and a back-up roll (251D) as shown in FIG. 9. The glue (G) in the glue pan (251A) is transferred by the distribution roll (251B) to the patterned roll (251C) which has sculptured patterns on its surface. The glue patterns are fixed by the sculptured patterns on the patterned roll (251C) like a stamp. I.e., the glue patterns correspond to the sculptured patterns on the surface of the patterned roll (251C). Alternatively, any other known method to apply glue may be used. One of or both of the distribution roll (251B) and/or the patterned roll (251C) are biased toward each other at the nip between the rolls (251B) and (251C). Furthermore, one of or both of the patterned roll (251C) and/or the back-up roll (25 ID) are also biased toward each other at the nip between the rolls (251C) and (251D). By feeding the continuous flange material (211')

to the nip between the rolls (251C) and (251D), the glue transferred to the patterned roll (251C) is applied onto the adhesive flange part (232) of the continuous flange material (211'). Then the continuous flange material (211') is fed toward the perforating step (260) along MD1.

Figure 10:
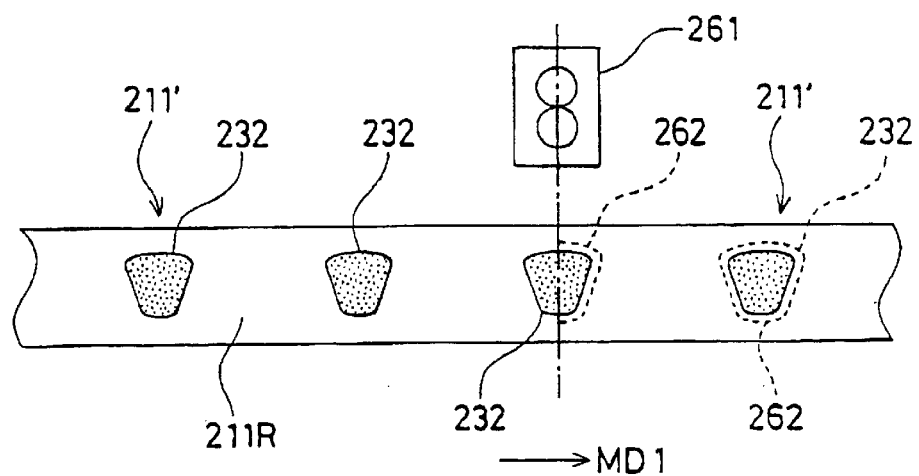
FIG. 10 is a fragmentary plan view of the release film perforating step which is a part of the process in FIG. 5.

The release film perforating step (260) may include a perforating unit (261). In the release film perforating step (260), the continuous flange material (211') is forwarded to the perforating unit (261) and is perforated along an outline (262) of the final shape of the release film layer (211R) as shown in FIG. 10. Preferably, the final shape of the release film layer (211R) is slightly larger than the adhesive flange part (232). The perforating unit (261) may have a conventional perforating cutter having a die cutter. Alternatively, any other known method to cut may be used. It is important that this step is not a complete cutting step but a perforating step. This keeps the adhesive flange part (232) stay on the continuous flange material (211') after this step. Then the continuous flange material (211') is fed toward the release film trimming step (270) along MD1.

Figure 11:
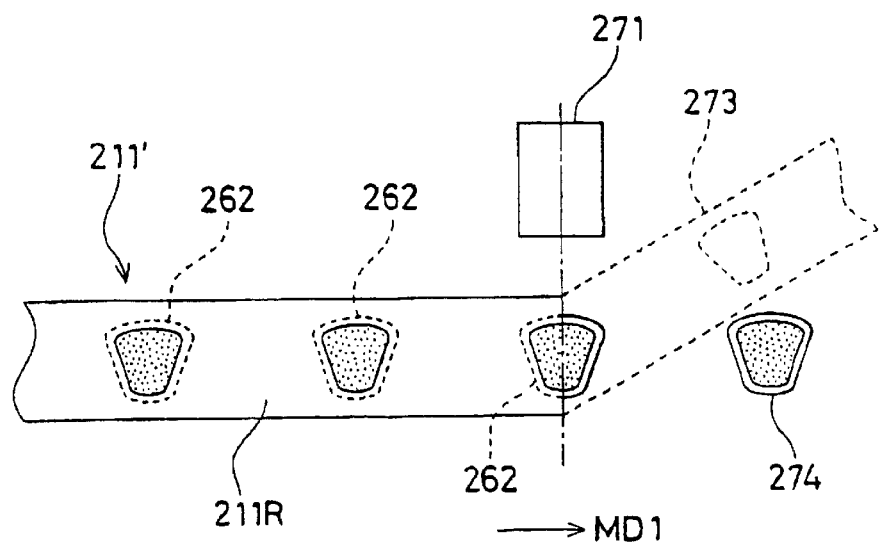
FIG. 11 is a fragmentary plan view of the release film trimming step which is a part of the process in FIG. 5.

The release film trimming step (270) may include a punching unit (271) and a turn drum (272) as shown in FIG. 5. In the release film trimming step (270), the release film layer (211R) is stamped by punching unit (271) along the perforation (262) which is formed in the perforating step (260), and then an unnecessary part (273) is trimmed as shown in FIGS. 5 and 11. Then the discrete final adhesive flanges (274) which is the rest of parts except the unnecessary part (273) are fed to the turn drum (272), and the feeding speed of the discrete final adhesive flanges (274) is synchronized with the body facing sheet feeding speed on the turn drum unit (272) because the flange material feeding speed is different from the body facing sheet feeding speed (refer to FIG. 12). Preferably, the body facing sheet feeding speed is faster than the flange material feeding speed. In addition, the discrete final adhesive flanges (274) may be rotated 90 degrees on the turn drum unit (272) on the way to the flange joining step (320). Then the discrete final adhesive flanges (274) arranged to provide a predetermined interval are fed toward the flange joining step (320).

The body facing sheet making section (300) comprises nine steps, a body facing sheet material feeding step (310), a flange joining step (320), an opening punching step (330), an opening inner edge treatment step (340), a second release film joining step (350), a Z-folding step (360), a Z-fold pre-bonding step (370), an OMEGA-folding step (380) and an OMEGA-fold pre-bonding step (390).

The body facing sheet material feeding step (310) continuously feeds an unwound body facing sheet material (311) toward the flange joining step (320) along MD2. The continuous body facing sheet material (311) preferably comprises liquid-impermeable material.

Figure 12:
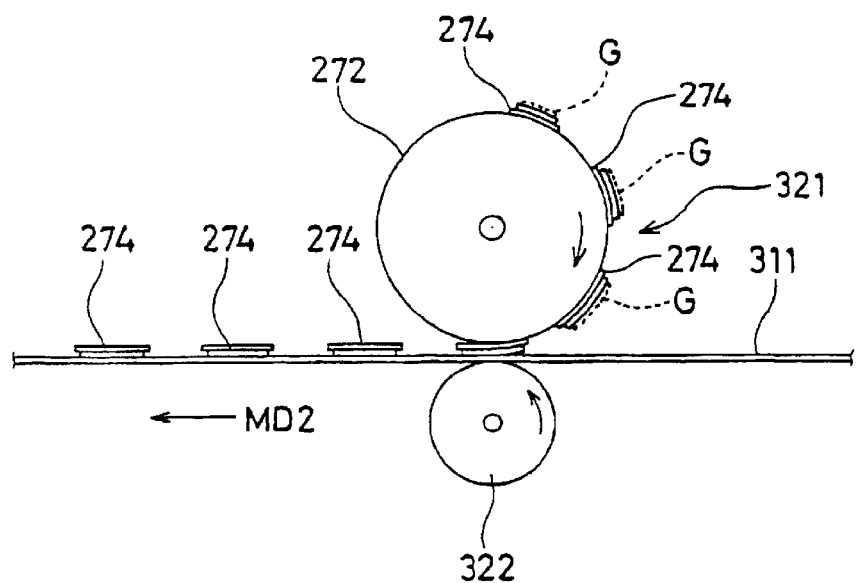
FIG. 12 is a fragmentary, schematic side elevational view of the flange joining unit shown in FIG. 5.

The flange joining step (320) joins the continuous body facing sheet material (311) and the discrete final adhesive flanges (274) by the flange joining unit (321). The joining unit (321) may comprise the turn drum (272) and a pressing roll (322) as shown in FIGS. 5 and 12. One of or both of the turn drum (272) and/or the pressing roll (322) are biased toward each other at the nip between the turn drum (272) and the pressing roll (322). By feeding the continuous body facing sheet material (311) and the adhesive flange (274) with the glue (G) which was applied in the glue applying step (250) to the nip of the joining unit (321) as shown in FIG. 12, the continuous body facing sheet material (311) and the adhesive flange (274) are joined at the right position as shown in FIG. 5. Then the continuous body facing sheet material (311) is fed to the opening punching step (330) along MD2.

Figure 13:
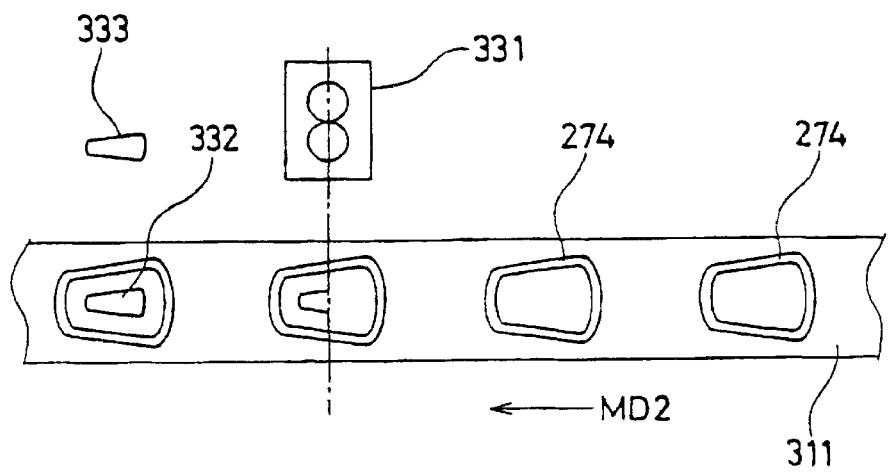
FIG. 13 is a fragmentary plan view of the opening punching step which is a part of the process in FIG. 5.

The opening punching step (330) may include a punching unit (331). In the opening punching step (330), the continuous body facing sheet material (311) is forwarded to the punching unit (331) and is punched an opening (332) in both the web (311) and the adhesive flange (274), and then the unnecessary part (333) is trimmed as shown in FIGS. 5 and 13. The outline of the opening (332) corresponds to the inner periphery (12B) in FIG. 1. The opening punching unit (331) may be a conventional cutter (or puncher) having a die cutter. Alternatively, any other known method to cut (or punch) may be used. The continuous body facing sheet material (311) is then fed toward the opening inner edge treatment step (340) along MD2.

Figure 14A:
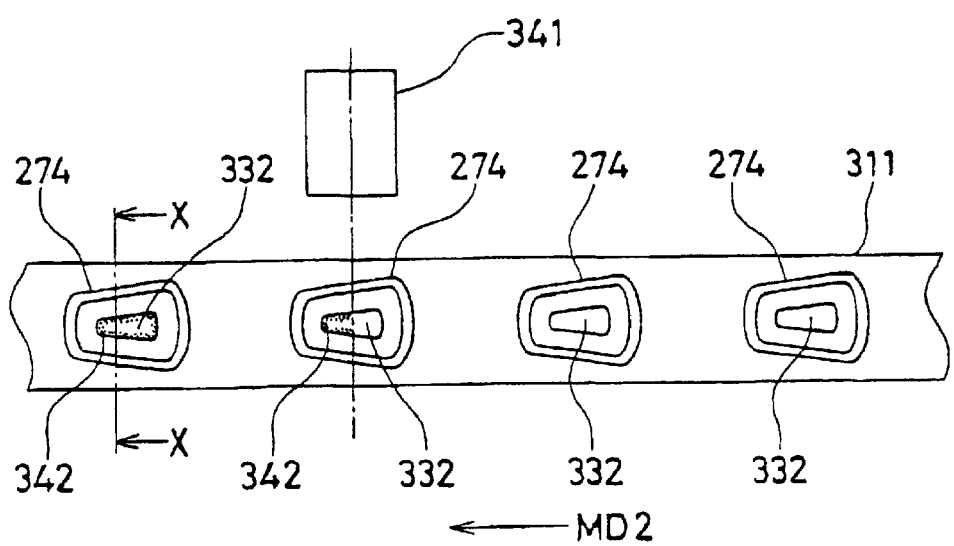
FIG. 14A is a fragmentary plan view of the opening inner edge treatment step which is a part of the process in FIG. 5.
Figure 14B:
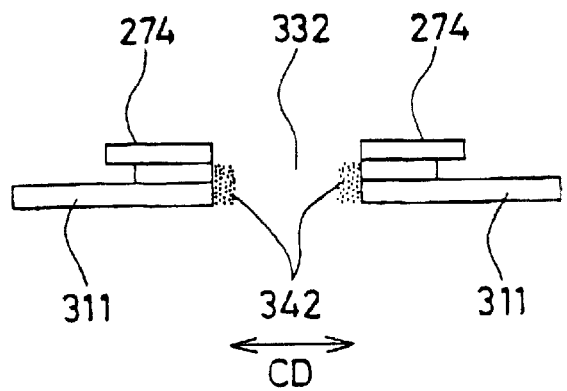
FIG. 14B is a cross-sectional view taken along line X—X of FIG. 14A.

The opening inner edge treatment step (340) applies a coating to coat the periphery edge of the opening (332) with hydrophobic material (342) by a coating unit (341) as shown in FIGS. 14A and 14B. It is possible that the hydrogel adhesive contact to urine (or other excreta) during usage of the device, such as the disposable urine management device (10) of the present invention. This may aggravate the property of the hydrogel adhesive due to its emulsification. Therefore, the periphery edge of the opening (332) of such device preferably needs to be coated with the hydrophobic material (342) as shown in FIG. 14B such that the hydrogel adhesive is protected from urine. It is preferable that the hydrophobic material (342) is a hydrophobic skin adhesive. Preferably, such hydrophobic material (342) comprises hydrogenated Styrene Isoprene Block, Petroleum Hydrocarbon resin, Paraffin Oil, and Antioxidant. Alternatively, any other known hydrophobic skin adhesives may be used. As for one example of the coating method, the coating point of the periphery edge of the opening (332) is charged by the charging plate and then is coated the opposite polarized hydrophobic material by spray gun. Alternatively, any other known method to coat may be used. The continuous body facing sheet material (311) is then fed toward the second release film joining step (350) along MD2.

Figure 15:
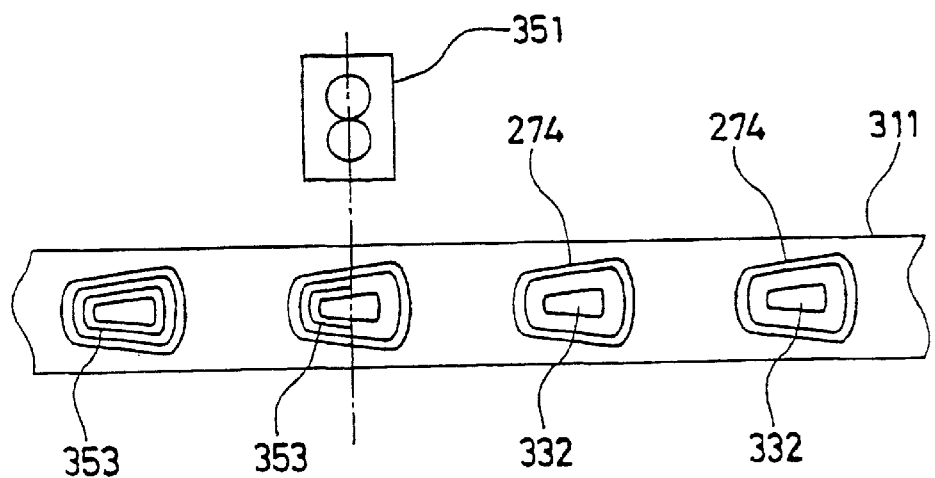
FIG. 15 is a fragmentary plan view of the second release film joining step which is a part of the process in FIG. 5.

The second release film joining step (350) attaches the second release film to the continuous body facing sheet material (311) in order to cover the opening (332) formed in the opening punching step (330) so that foreign objects do not enter into the bag (11) before use of the device (10). The second release film joining step (350) may include a second release film joining unit (351). The continuous second release film web (352) is fed toward the second release film joining unit (351) as shown in FIG. 5. The continuous second release film web (352) is cut into a discrete segment having a final second release film shape and is applied glue on the way to the second release film joining unit (351). Finally, The second release film (353) is attached on the position of the opening (332) of the continuous body facing sheet material (311) at the second release film joining unit (351) as shown in FIGS. 5 and 15. Then the continuous body facing sheet material (311) is fed toward the Z-folding step (360) along MD2.

Figure 16:
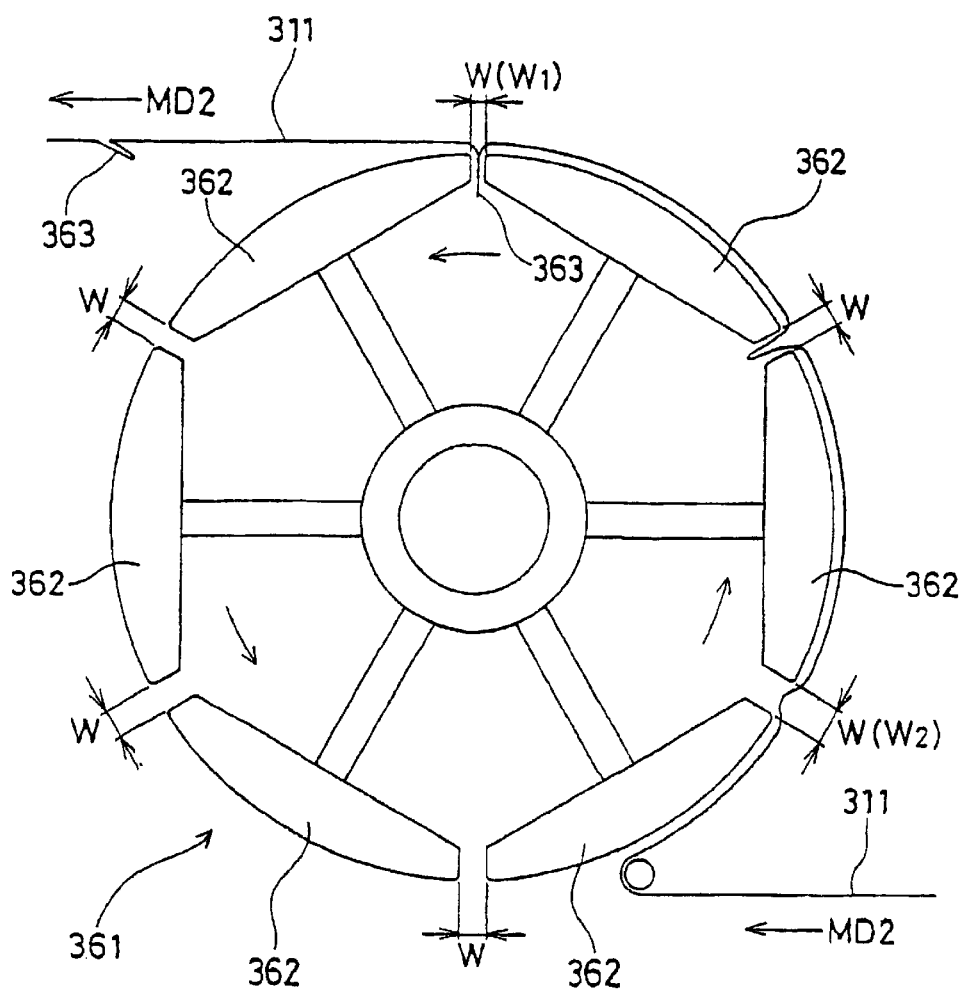
FIG. 16 is a fragmentary, schematic side elevational view of the Z-folding unit shown in FIG. 5.

The Z-folding step (360) forms Z-folds on the surface of the continuous body facing sheet material (311) by a Z-folding unit (361). The Z-folding unit (361) may include plural folding assemblies (362) arranged to provide an interval (W) as shown in FIG. 16. In this embodiment, the folding unit (361) has six folding assemblies (362). The number of folding assemblies (362) will obviously depend upon the circumstances. All the folding assemblies (362) rotate coaxially and the interval (W) between adjoining folding assemblies (362) constantly changes from the minimum interval ($W_1$) to the maximum interval ($W_2$) while the Z-folding unit (361) is rotating. The continuous body facing sheet material (311) is fed to the Z-folding unit (361), and then each Z-fold (363) is formed on the surface of the continuous body facing sheet material (311) by pinching the web (311) between adjoining folding assemblies (362) as shown in FIG. 16. The interval (W) become the maximum interval ($W_2$) when the continuous body facing sheet material (311) approaches and reaches to the Z-folding unit (361) so that the continuous body facing sheet material (311) can enter between adjoining folding assemblies (362). The interval (W) become the minimum interval ($W_1$) when the Z-fold (363) is completely formed on the continuous body facing sheet material (311). There are preferably predetermined intervals between the adjoining Z-folds on the continuous body facing sheet material (311). Alternatively, any other known method to form Z-folds on the continuous material may be used. Then the continuous body facing sheet material (311) is fed toward the Z-fold pre-bonding step (370) along MD2.

The Z-fold pre-bonding step (370) temporarily may bond the Z-folds (363) at the several points (363A) on the continuous body facing sheet material (311) as shown in FIG. 5. This step helps to maintain the Z-folds (363) after the Z-folding step (360). Because the continuous body facing sheet material (311) always is under tension along MD2 during manufacturing, this is important step for manufacturing of the devices such as the disposable urine management device which has any folds like the Z-fold. Then the continuous body facing sheet material (311) is fed toward the OMEGA-folding step (380) along MD2.

Figure 17A:
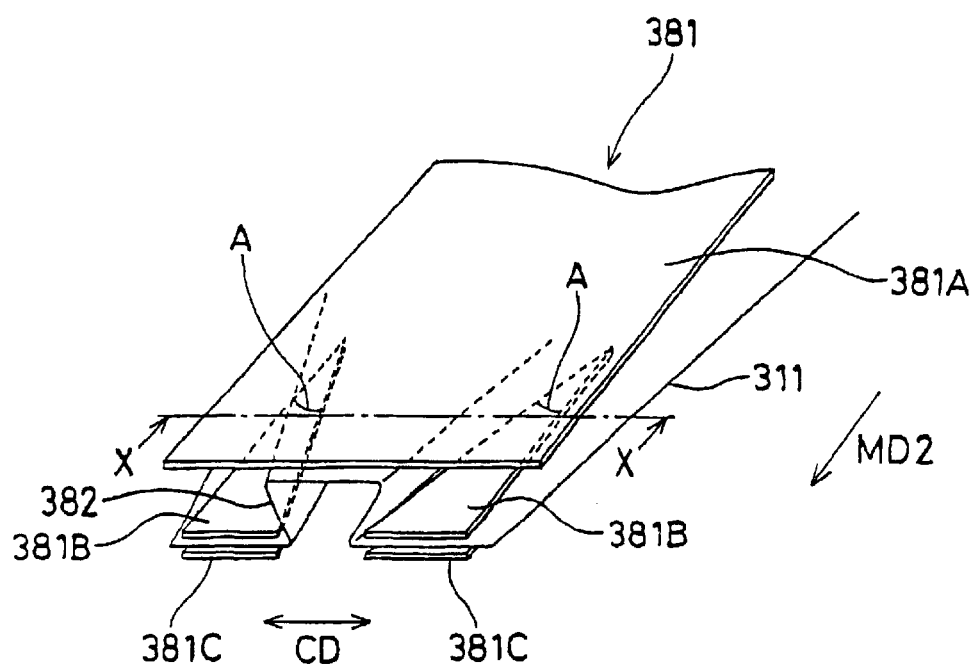
FIG. 17A is a fragmentary perspective view of the OMEGA-folding unit shown in FIG. 5.
Figure 17B:
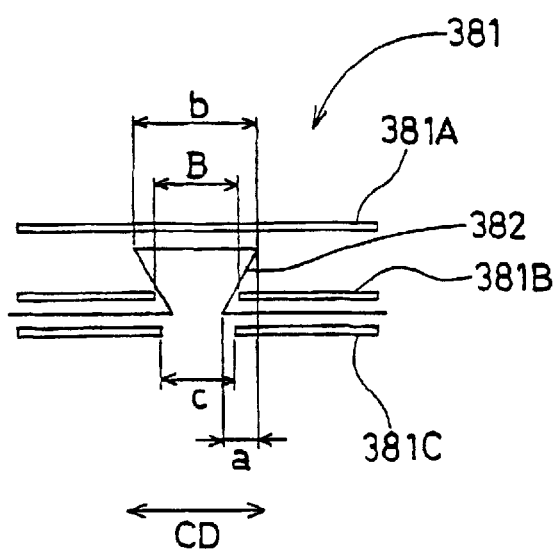
FIG. 17B is a cross-sectional view taken along line X—X of FIG. 17A.

The OMEGA-folding step (380) forms OMEGA-folds on the surface of the continuous body facing sheet material (311) by a OMEGA-folding unit (381). The OMEGA-folding unit (381) may include a support plate (381A), a pair of first folding plates (381B) arranged to provide a predetermined spacing (B) along CD therebetween, and a pair of second folding plates (381C) arranged to provide a predetermined spacing (C) along CD therebetween as shown in FIGS. 17A and 17B. By feeding the continuous body facing sheet material (311) to the OMEGA-folding unit (381), the OMEGA-fold (382) (i.e. two parallel Z-folds in opposition to each other along MD2) is formed on the surface of the continuous body facing sheet material (311) as shown in FIGS. 17A and 17B. It is possible to adjust the width designated by the reference number (b) in FIG. 17B by adjusting the spacing (B) between the first folding plates (381B). Furthermore, it is possible to adjust the width designated by the reference number (a) in FIG. 17B by adjusting the angle designated by the reference number (A) in FIG. (18A). Alternatively, any other known method to form OMEGA-fold on the continuous material web may be used. Then the continuous body facing sheet material (311) is fed toward the OMEGA-fold pre-bonding step (390) along MD2.

The OMEGA-fold pre-bonding step (390) temporarily may bond the OMEGA-folds at the several points (382A) on the continuous body facing sheet material (311) as shown in FIG. 5. This step helps to maintain the OMEGA-fold (382) after the OMEGA-folding step (380). Because the continuous body facing sheet material (311) always is under tension along MD2 during manufacturing, this is important step for manufacturing of the devices such as the disposable urine management device which has any folds like the OMEGA-fold. Then the continuous body facing sheet material (311) is fed toward the body facing sheet-garment facing composite web joining step (510) along MD2.

By forming OMEGA-fold after Z-fold, it is possible for the disposable urine management device (10) of the present invention to provide extra storage capacity effectively. In other words, the disposable urine management device can expand vertically to have a 3-dimentional shape in use, with the result that it is possible for the wear period of such a device to become longer. Therefore, the order to form "Z and OMEGA"-folds is an important characteristic in a disposable excreta management device having a plurality of folds on the surface of its bag. In addition, to form OMEGA-fold after Z-fold on the continuous body facing sheet material (311) may proceed before the above mentioned flange joining step (320) or anytime between the flange joining step (320) and the body facing sheet joining step (510).

The absorbent material making section (400) comprises three steps, an absorbent material feeding step (410), an absorbent material cutting step (420), and a main body assembling step (430).

Figure 18:
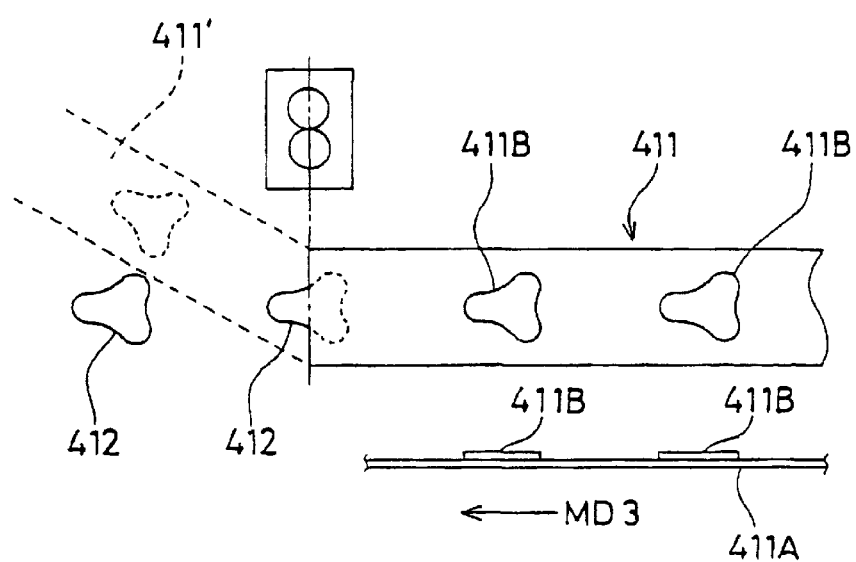
FIG. 18 is a fragmentary plan view of the absorbent material cutting step which is a part of the process in FIG. 5.

The absorbent material feeding step (410) continuously feeds an unwound composite absorbent material web (411) toward the absorbent material cutting step (420) along MD3. The composite absorbent material web (411) comprises a carrier web (411A) and discrete absorbent cores (411B) as shown in FIG. 18.

The absorbent material cutting step (420) may include a cutting unit (421). The continuous composite absorbent material web (411) is forwarded to the cutting unit (421) and is cut into a discrete segment having a final shape of an absorbent material (i.e., a discrete composite absorbent material (412)) as shown in FIG. 18, and then the unnecessary part (411') is trimmed as shown in FIG. 18. The cutting unit (421) may be a conventional cutter having a die cutter. Alternatively, any other known method to cut may be used. Then the discrete composite absorbent materials (412) are fed individually toward main body assembling step (430) along MD3.

The main body assembling step (430) superposes the discrete composite absorbent materials (412) on a continuously formed garment facing sheet material web (413), furthermore, a continuous liquid permeable topsheet material (414) is superposed on both the discrete composite absorbent material (412) and the continuous garment facing sheet material (413). Accordingly, the discrete composite absorbent materials (412) are placed between the continuous liquid permeable topsheet material (414) and the continuous garment facing sheet material (413). Preferably, the feeding speeds of each of the materials (412), (413) and (414) are synchronized each other at the same time in (or before) this step (430). A continuous garment facing composite web (415), which consists of the continuous liquid permeable topsheet material (414), the discrete composite absorbent materials (412) and the continuous garment facing sheet material (413), is made by this step (430). Then the continuous garment facing composite web (415) is fed toward the body facing sheet joining step (510) along MD3.

The final product making section (500) comprises two steps, a body facing sheet joining step (510) and a final cutting step (520).

Figure 19A:
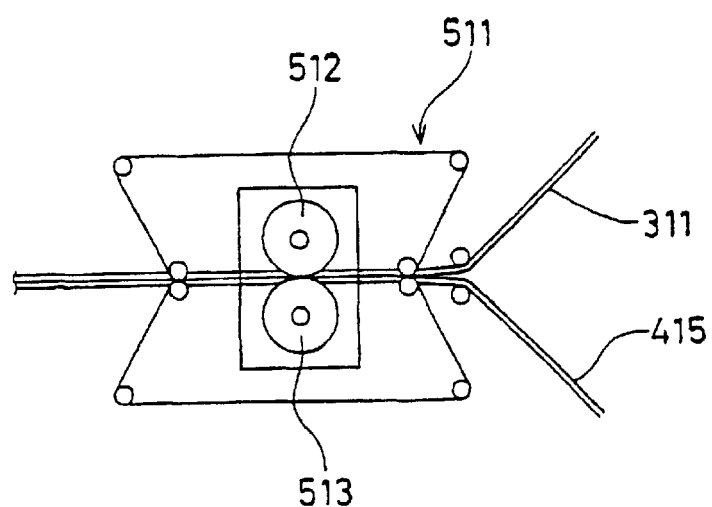
FIG. 19A is a fragmentary, schematic side elevational view of the chassis sealing unit shown in FIG. 5.
Figure 19B:
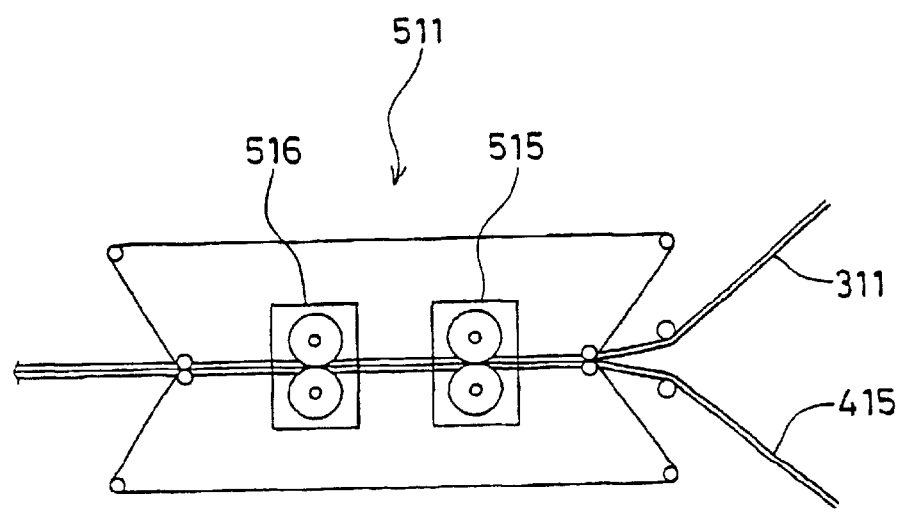
FIG. 19B is a fragmentary, schematic side elevational view of an alternative embodiment of the chassis sealing unit shown in FIG. 5.

The body facing sheet joining step (510) joins the continuous body facing sheet material (311) and the continuous garment facing composite web (415) by the chassis sealing unit (511). The chassis sealing unit (511) may comprise a roll (512) and a roll (513) as shown in FIG. 19A. One of or both of the roll (512) and/or the roll (513) are biased toward each other at the nip between the rolls (512) and (513). By feeding the continuous body facing sheet material (311) and the continuous garment facing composite web (415) to the nip of the chassis sealing unit (511) and then by applying pressure and/or heat, the continuous body facing sheet material (311) and the continuous garment facing composite web (415) are bonded together along the periphery (514) of the final shape (600) of the disposable urine management device (10) as shown in FIG. 5. In this step (510), the Z-fold (363) and the OMEGA-fold (382) are also bonded along the periphery (514) of the final shape (600) of the device (10). In the other preferred embodiment, the chassis sealing unit (511) may include a first unit (515) and a second unit (516) as shown in FIG. 19B. In the embodiment, by feeding the continuous body facing sheet material (311) and the continuous garment facing composite web (415) to the nip of the first unit (515) and then by applying pressure and/or heat, the continuous body facing sheet material (311) and the continuous garment facing composite web (415) are bonded together along the periphery (514) of the final shape (600) of the disposable urine management device (10) (this step also includes preliminary bonding about Z-fold (363) and OMEGA-fold (382)); and then, by feeding the continuous body facing sheet material (311) and the continuous garment facing composite web (415) to the nip of the second unit (516) and then by applying pressure and/or heat, the Z-fold and the OMEGA-fold are also bonded completely along the periphery (514) of the final shape (600) of the device (10). Then the continuous body facing sheet material (311) and the continuous garment facing composite web (415) are fed toward the final cutting step (520) along MD2.

The final cutting step (520) may include a cutting unit (521). The continuous body facing sheet material (311) and the continuous garment facing composite web (415) are forwarded to the final cutting unit (521) and are cut into a discrete segment having a final shape (i.e., discrete compound disposable urine management device (10)) and then the unnecessary part (522) is trimmed. The cutting unit (521) may be a conventional cutter having a die cutter. Alternatively, any other known method to cut may be used.

Figure 20B:
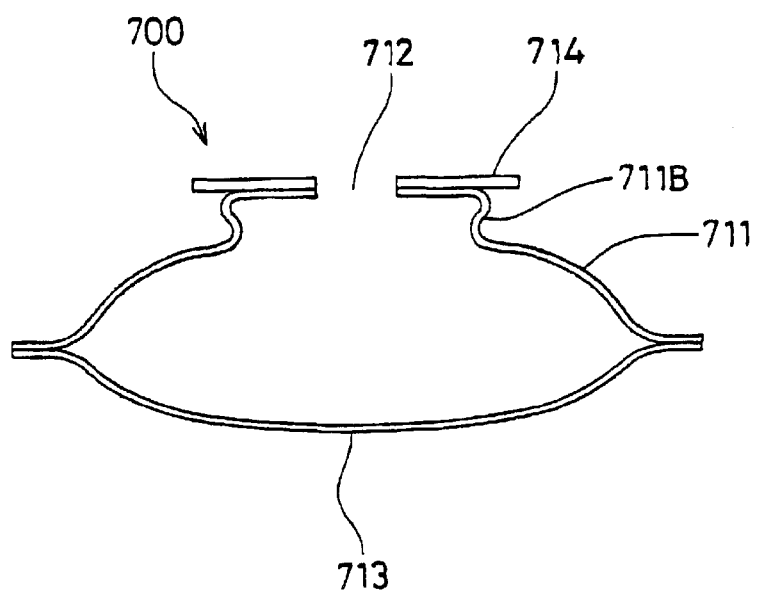
FIG. 20B is a cross-sectional view taken along line X—X of FIG. 20A.

Although the embodiment above described is about a disposable urine management device, the present invention can be also applied to a method for manufacturing other excreta (e.g. bowel movement) management devices (700) as shown in FIG. 20A. In the embodiment, the device (700) has a longitudinal centerline (Lo) and a lateral centerline (La), furthermore, has a body facing surface and a garment facing surface. The device (700) comprises a liquid impermeable body facing sheet (711) having an opening (712), a liquid impermeable garment facing sheet (713), an adhesive flange (714) being placed at periphery of the opening (712) for releasable attachment to the body of the wearer. The Z-fold (711A) and OMEGA-fold (711B) are formed on the surface of the liquid impermeable body facing sheet (711). However, the device (700) does not have an absorbent material unlike the above-mentioned disposable urine management device (10) as shown in FIG. 20B. Therefore, in the manufacturing step of the device (700), the step about an absorbent material is missed in the above-mentioned step for manufacturing the disposable excreta management device (10). The other steps are basically identical to the previously described embodiment.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a disposable excreta management device having a longitudinal centerline, a lateral centerline, a body facing surface and a garment facing surface, the disposable excreta management device comprising a liquid impermeable body facing sheet having an opening, a liquid impermeable garment facing sheet, an adhesive flange provided adjacent to the opening for releasable attachment to the body of the wearer, the adhesive flange comprising a substrate layer and an adhesive layer, the liquid impermeable body facing sheet having plural folds thereon, the plural folds comprising at least one lateral fold and at least a pair of longitudinal folds, the method comprising the steps of:

(a) combining a continuous liquid impermeable body facing sheet web and a discrete adhesive flange to make a first continuous composite web at a first combining section, (b) forming a lateral fold on the continuous liquid impermeable body facing sheet web at a first fold forming section and a pair of longitudinal folds on the continuous liquid impermeable body facing sheet web at a second fold forming section subsequent to the first fold forming section, (c) combining the first continuous composite web and a continuous liquid impermeable garment facing sheet web to make a second continuous composite web at a second combining section, and (d) cutting the second continuous composite web into the discrete disposable excreta management device.

2. The method of claim 1 wherein the compound disposable excreta management device is an urine management device comprising an absorbent material placed between the liquid impermeable body facing sheet and the liquid impermeable garment facing sheet, and a liquid permeable topsheet being placed between the liquid impermeable body facing sheet and the absorbent material.

3. The method of claim 1 further includes the step of coating the periphery edge of the opening with hydrophobic material.

4. The method of claim 3 wherein the hydrophobic material comprises hydrogenated Styrene Isoprene Block, Petroleum Hydrocarbon resin, Paraffin Oil, and Antioxidant.

5. The method of claim 1 wherein the combining step at the second combining section includes the step of applying pressure and/or heat along the periphery of the disposable excreta management device.

6. The method of claim 5 wherein the lateral and/or longitudinal folds are bonded at predetermined several spots on the first continuous composite web in the combining step at the second combining section.

7. The method of claim 1 wherein the forming step proceeds before the combining step at the first combining section.

8. The method of claim 1 wherein the forming step proceeds after the combining step at the first combining section.

9. A disposable excreta management device having a longitudinal centerline, a lateral centerline, a body facing surface and a garment facing surface, the disposable excreta management device comprising a liquid impermeable body facing sheet having an opening, a liquid impermeable garment facing sheet, an adhesive flange provided adjacent to the opening for releasable attachment to the body of the wearer, the adhesive flange comprising a substrate layer and an adhesive layer, the liquid impermeable body facing sheet having plural folds thereon, the plural folds comprising at least one lateral fold and at least a pair of longitudinal folds, made according to the method comprising the steps of;

(a) combining a continuous liquid impermeable body facing sheet web and a discrete adhesive flange to make a first continuous composite web at a first combining section, (b) forming a lateral fold on the continuous liquid impermeable body facing sheet web at a first fold forming section and a pair of longitudinal folds on the continuous liquid impermeable body facing sheet web at a second fold forming section subsequent to the first fold forming section, (c) combining the first continuous composite web and a continuous liquid impermeable garment facing sheet web to make a second continuous composite web at a second combining section, and (d) cutting the second continuous composite web into the discrete disposable excreta management device.

* * * * *